United States Patent
Alexander et al.

(10) Patent No.: US 11,603,565 B2
(45) Date of Patent: Mar. 14, 2023

(54) SYSTEM FOR IDENTIFICATION OF ANTIGENS RECOGNIZED BY T CELL RECEPTORS EXPRESSED ON TUMOR INFILTRATING LYMPHOCYTES

(71) Applicants: Roche Sequencing Solutions, Inc., Pleasanton, CA (US); Ventana Medical Systems, Inc., Tucson, AZ (US)

(72) Inventors: Nelson R. Alexander, Marana, AZ (US); Aoune Barhoumi, Oro Valley, AZ (US); Jan Berka, Pleasanton, CA (US); Rui Chen, Fremont, CA (US); Lisa L. Gallegos, Tucson, AZ (US); Toumy Guettouche, Pleasanton, CA (US); Seoyoung Kim, Foster City, CA (US); Maeve E. O'Huallachain, Belmont, CA (US); Sedide Ozturk, Pleasanton, CA (US); Jigar Patel, Verona, WI (US); Florian Rubelt, Menlo Park, CA (US); Stacey Stanislaw, Tucson, AZ (US)

(73) Assignees: ROCHE SEQUENCING SOLUTIONS, INC., Pleasanton, CA (US); VENTANA MEDICAL SYSTEMS, INC., Oro Valley, AZ (US)

( * ) Notice: Subject to any disclaimer, the term of this patent is extended or adjusted under 35 U.S.C. 154(b) by 88 days.

(21) Appl. No.: 17/252,222

(22) PCT Filed: Jun. 14, 2019

(86) PCT No.: PCT/EP2019/065717
§ 371 (c)(1),
(2) Date: Dec. 14, 2020

(87) PCT Pub. No.: WO2019/238939
PCT Pub. Date: Dec. 19, 2019

(65) Prior Publication Data
US 2021/0285049 A1 Sep. 16, 2021

Related U.S. Application Data

(60) Provisional application No. 62/685,469, filed on Jun. 15, 2018.

(51) Int. Cl.
| | |
|---|---|
| *C12Q 1/6883* | (2018.01) |
| *C12N 15/10* | (2006.01) |
| *C12Q 1/6806* | (2018.01) |
| *C12Q 1/6881* | (2018.01) |

(52) U.S. Cl.
CPC ....... *C12Q 1/6883* (2013.01); *C12N 15/1034* (2013.01); *C12Q 1/6806* (2013.01); *C12Q 1/6881* (2013.01)

(58) Field of Classification Search
CPC .. C12Q 1/6883; C12Q 1/6881; C12Q 1/6806; C12N 15/1034; G01N 33/56977
See application file for complete search history.

(56) References Cited

FOREIGN PATENT DOCUMENTS

| WO | 2015/185067 A1 | 12/2015 |
|---|---|---|
| WO | 2016100977 A1 | 6/2016 |
| WO | 2016196691 A2 | 12/2016 |
| WO | 2017013170 A1 | 1/2017 |
| WO | 2018/057051 A1 | 3/2018 |

OTHER PUBLICATIONS

Han et al., Nat. Biotechnol., 32(7): 684-692, Jul. 2014.*
Bentzen et al., Nature Biotechnology, 34(10): 1037-1048, Aug. 2016.*
Birnbaum, M et al., Deconstructing the Peptide-MHC Specificity of T Cell Recognition, Cell, (2014), pp. 1073-1087, vol. 157, Issue 5.
International Search Report and Written Opinion, dated Aug. 6, 2019, in corresponding PCT/EP2019/065717, filed Jun. 14, 2019, pp. 1-14.

* cited by examiner

*Primary Examiner* — Cynthia B Wilder
(74) *Attorney, Agent, or Firm* — Eric Grant Lee; Olga Kay

(57) ABSTRACT

The invention is a method of identifying a cognate antigen for a T-cell receptor using neoantigens from a patient's tumor cells combined with the patient's T-cells and using cell sorting, genome sequencing, expressing TCR genes, presenting tumor neoantigens on MHC complex and uniquely barcoding the T-cells where TCR recognition occurs to tag all components of the TCR recognition complex.

15 Claims, 4 Drawing Sheets

SYSTEM FOR IDENTIFICATION OF ANTIGENS RECOGNIZED BY T CELL RECEPTORS EXPRESSED ON TUMOR INFILTRATING LYMPHOCYTES

FIELD OF THE INVENTION

The invention relates to the field of immunology and tumor antigens and more specifically, to the use of combinatorial barcoding to identify anti-tumor immune cells and tumor antigens.

BACKGROUND OF THE INVENTION

T-cells are integral to the adaptive immune system and provide protection against pathogens and cancer. They function through extracellular recognition of antigens by the T-cell receptor (TCR), which displays specific affinity to short peptides presented on the human leukocyte antigen (HLA) encoded MHC (major histocompatibility complex) structure on antigen presenting cells. Diversity inherent to the TCR, peptide, and MHC molecules makes identifying the specificity of any one TCR an extremely complex problem, Gee, M. H., et al., *Antigen Identification for Orphan T Cell Receptors Expressed on Tumor-Infiltrating Lymphocytes*. Cell, 2017. While technologies that enable molecular characterization of T-cells and their TCR sequences have improved considerably, the ability to determine and study the antigen specificities of T-cells has remained a major bottleneck. Approaches to determining the specificity of "orphan" TCRs (i.e., TCRs of unknown antigen specificity) could help uncover potential targets for cancer immunotherapy, autoimmunity, and infection, see Gee, supra. A number of strategies have been used to determine the specificity of "orphan" TCRs, see Birnbaum, M. E., et al., *Deconstructing the peptide-MHC specificity of T cell recognition*. Cell, 2014. 157(5): p. 1073-87. Mass spectrometry can provide an unbiased method of antigen isolation Yadav, M., et al., *Predicting immunogenic tumour mutations by combining mass spectrometry and exome sequencing*. Nature, 2014. 515(7528): p. 572-6, but requires large cell numbers, typically $10^1$ to $10^1$ cells. Most studies of T-cell antigen specificities involve testing candidate antigens empirically. For example, studies of anti-tumor T-cell specificities have shown productive T-cell responses toward neoantigens. Such studies entail sequencing tumors to identify mutations, using epitope prediction algorithms to predict immunogenic mutant peptides and testing for T-cell responses directed at these mutant peptides, see Zolkind, P., et al., *Neoantigens in immunotherapy and personalized vaccines: Implications for head and neck squamous cell carcinoma*. Oral Oncology, Snyder, A. and T. A. Chan, Immunogenic peptide discovery in cancer genomes. Current Opinion in Genetics & Development, 2015. 30(0): p. 7-16. Other strategies query established T-cell specificities in patients by using pHLA multimers Leong, M. L. and E. W. Newell, *Multiplexed Peptide-MHC Tetramer Staining with Mass Cytometry*. Methods Mol Biol, 2015. 1346: p. 115-31, Newell, E. W. and M. M. Davis, *Beyond model antigens: high-dimensional methods for the analysis of antigen-specific T cells*. Nat Biotechnol, 2014. 32(2): p. 149-57.

There remains a need to connect each unique T-cell receptor to the peptide sequences it recognizes. Of special interest identification and matching of tumor-derived peptides and antitumor T-cells.

SUMMARY OF THE INVENTION

In one embodiment, the invention is a method of identifying a cognate antigen for a T-cell receptor (TCR) composed of an alpha chain (TCRα) and a beta chain (TCRβ), the method comprising: obtaining a population of T-cells from a patient wherein each T-cell comprises a TCR comprising TCRα and TCRβ chains; barcoding nucleic acids from each T-cell with a cell-specific barcode; sequencing the barcoded nucleic acids to obtain TCRA and TCRB gene sequences coding for the TCRα and TCRβ chains; identifying TCRA and TCRB genes having the same barcodes as gene pairs encoding a functional TCR; introducing the TCRA and TCRB gene pairs into a receptive T-cell; obtaining a population of tumor cells from the patient each possibly comprising one or more tumor neoantigen; identifying tumor neoantigen genes; forming neoantigen peptides from the neoantigen genes; combining the neoantigen peptides with an MHC-1 antigen presenting complex and an oligonucleotide barcode to form a barcoded MHC-neoantigen peptide complex; contacting the transfected T-cells with the barcoded MHC-neoantigen peptide complexes to form cell-bound MHC-neoantigen-TCR complexes; barcoding the TCR genes and the MHC-neoantigen complex barcode from each T-cell with a cell-specific barcode; sequencing the TCR genes with associated cell-specific barcodes and the MHC-neoantigen complex barcodes associated with cell-specific barcodes in the T-cells; identifying the neoantigen as the cognate antigen for the TCR if at least one of the TCR genes and MHC-neoantigen complex barcode are associated the same cell-specific barcode.

The T-cells may be obtained by dissociation of tumor tissue. The TCRA and TCRB gene sequences coding for the TCRα and TCRβ chains can be rearranged DNA sequences or RNA sequences.

The population of T-cells is obtained from the tumor by protein marker expression based capture, such as fluorescence activated cell sorting (FACS). The T-cells can be selected as $CD3^+/CD8^+/TCR^+$ T-cells, as $CD45RA^+$ $CD45RO^-$ $CCR7^+CD62L^+$ naïve T cells, as $CD45RA^-$ $CD45RO^+CCR7^+CD62L^+$ central memory T cells, as $CD45RA^-CD45RO^+CCR7^-CD62L^-$ effector memory T cells, as $CD45RA^+CD45RO^-CCR7^-CD62L^-$ effector T-cells, or as $CD4^+CD25^+FoxP3^+$ regulatory T-cells.

In some embodiments, the T-cell barcoding is performed by a method comprising contacting the plurality of T-cells with a mixture of primers comprising a gene-specific sequence and a barcode oligonucleotide annealing region; and contacting the plurality of T-cells with barcode oligonucleotides complementary to the barcode oligonucleotide annealing region in the primer; contacting the plurality of T-cells with additional barcode oligonucleotides in each of one or more rounds of split pool synthesis wherein the barcoded oligonucleotide in each round comprises an annealing region complementary to the annealing region of the barcode oligonucleotide from the previous round, thereby assembling cell-specific barcodes on each primer in each of the plurality of T-cells. The gene-specific sequence may be selected from TCRA, TCRB, CD3, CD4, CD8 and FoxP3.

In some embodiments, the T-cell barcoding is performed by a method comprising partitioning the population of T-cells containing nucleic acids into a plurality of first partitions containing a single cell; mixing the cell-containing partitions with a plurality of second partitions each containing multiple copies of barcoded oligonucleotide primers comprising a gene-specific sequence and a barcode, wherein the barcodes are the same within each partition but differ among partitions; fusing the first and second partitions; and forming amplicons with barcoded oligonucleotide primers thereby barcoding the nucleic acids. The gene-specific sequence may be selected from TCRA, TCRB, CD3, CD4, CD8 and FoxP3.

In some embodiments, the T-cell barcoding and sequencing are performed by a method comprising partitioning the population of T-cells into a plurality of partitions containing groups of cells; ligating barcoded adaptors to nucleic acids in each partition; sequencing the TCRA and TCRB in the adapted nucleic acids to obtain barcoded TCRA and TCRB sequences; determining TCRA and TCRB gene pairs base on frequency of co-occurrence in partitions.

The sequencing of barcoded TCR genes is sequencing the CDR3 hypervariable regions of the genes and identifying the TCR genes is identifying the CDR3 hypervariable regions of the genes.

In some embodiments, the neoantigen genes are identified by sequencing of the nucleic acids in the tumor cell and identifying genes with non-silent mutations as neoantigen genes. Sequencing may be whole genome sequencing or whole exome sequencing. The neoantigens may be identified is by sequence alignment. The neoantigens may also be identified by screening peptide arrays with a patient's serum.

In some embodiments, TCR genes may be introduced into receptive T-cells in expression vectors, e.g., vectors comprising one or both the TCRA and TCRB genes. The expression vectors may further comprise a vector expressing the CD3 protein and a vector expressing the CD8 protein. In some embodiments, the receptive T-cell lacks endogenous TCR genes expression.

In some embodiments, the genes are introduced into a receptive cell as transcriptionally active DNA fragments or as mRNA.

In some embodiments, the identified neoantigens are further selected by the ability to bind the MHC-I molecule. In some embodiments, the ability to bind the MHC-I molecule is determined by in silico analysis.

In some embodiments, the neoantigen peptides are 8-100 amino acids long. In some embodiments, the MHC-1 proteins have a patient-specific sequence.

In some embodiments, the MHC-neoantigen-TCR complexes are crosslinked after forming. In some embodiments, barcoding the neoantigen and the TCR in the neoantigen-TCR complex comprises compartmentalizing each complex into a reaction volume containing a barcode. In some embodiments, the sequencing steps in the method include massively parallel sequencing.

BRIEF DESCRIPTION OF THE DRAWINGS

FIG. 2A depicts steps 1-5 and FIG. 2B depicts steps 6 and 7.

DETAILED DESCRIPTION OF THE INVENTION

Definitions

Figure 1:
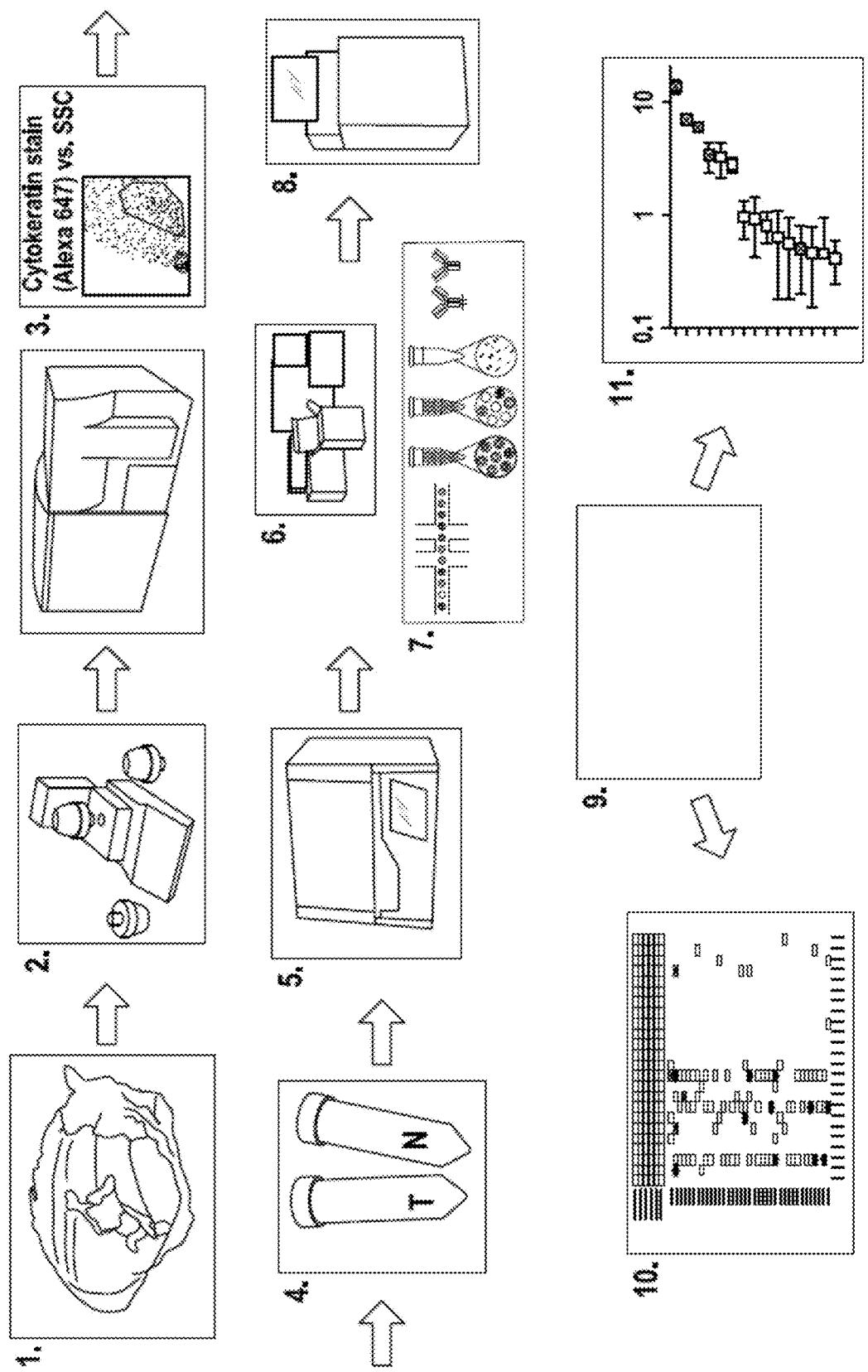
FIG. 1 shows a diagram of steps of the method from obtaining a tumor sample to generating ranked lists of neoantigens and T-cell receptor sequences. Examples indicated are arbitrary and therefore irrelevant in the context of the present application.

The following definitions aid in understanding of this disclosure.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA).

The term "nucleic acid" refers to polymers of nucleotides (e.g., ribonucleotides and deoxyribonucleotides, both natural and non-natural) including DNA, RNA, and their sub-categories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. Some examples of non-natural bases include those described in, e.g., Seela et al., (1999) Helv. Chim. Acta 82:1640, the contents of which are hereby incorporated by reference in its entirety. The non-natural bases may have a particular function, e.g., increasing the stability of the nucleic acid duplex, inhibiting nuclease digestion or blocking primer extension or strand polymerization.

The terms "polynucleotide" and "oligonucleotide" are used interchangeably. Polynucleotide is a single-stranded or a double-stranded nucleic acid. Oligonucleotide is a term sometimes used to describe a shorter polynucleotide. Oligonucleotides are prepared by any suitable method known in the art, for example, by a method involving direct chemical synthesis as described in Narang et al. (1979) Meth. Enzymol. 68:90-99; Brown et al. (1979) Meth. Enzymol. 68:109-151; Beaucage et al. (1981) Tetrahedron Lett. 22:1859-1862; Matteucci et al. (1981) J. Am. Chem. Soc. 103:3185-3191.

The term "primer" refers to a single-stranded oligonucleotide which hybridizes with a sequence in the target nucleic acid ("primer binding site") and is capable of acting as a point of initiation of synthesis along a complementary strand of nucleic acid under conditions suitable for such synthesis.

The term "adaptor" means a nucleotide sequence that may be added to another sequence so as to import additional properties to that sequence. An adaptor is typically an oligonucleotide that can be single- or double-stranded, or may have both a single-stranded portion and a double-stranded portion.

The term "ligation" refers to a condensation reaction joining two nucleic acid strands wherein a 5'-phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double-stranded molecule thus joining two double-stranded molecules. Ligation may also join two ends of a strand within a double-stranded molecule thus repairing a nick in the double-stranded molecule.

The term "barcode" refers to a nucleic acid sequence that can be detected and identified. Barcodes can be incorporated into various nucleic acids. Barcodes are sufficiently long e.g., 2, 5, 20 nucleotides, so that in a sample, the nucleic acids incorporating the barcodes can be distinguished or grouped according to the barcodes.

The term "multiplex identifier" or "MID" refers to a barcode that identifies a source of a target nucleic acids (e.g., a sample from which the nucleic acid is derived). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated.

The term "unique molecular identifier" or "UID" refers to a barcode that identifies a nucleic acid molecule to which it is attached. All or substantially all the target nucleic acid molecules from the same sample will have different UIDs. All or substantially all of the progeny (e.g., amplicons) derived from the same original target nucleic acid will share the same UID.

The term "quantum barcoding" or "QBC" refers to a process by which an individual cell in a mixture of cells can be labeled with a unique nucleic acid barcode the process comprising the steps of contacting the mixture of cells with a mixture of binding agents comprising a target-binding sequence and a barcode oligonucleotide annealing region; and contacting the cells with barcode oligonucleotides complementary to the barcode oligonucleotide annealing region in the binding agent; contacting the cells with additional barcode oligonucleotides in each of one or more rounds of split pool synthesis wherein the barcoded oligonucleotide in each round comprises an annealing region complementary to the annealing region of the barcode oligonucleotide from the previous round, thereby assembling cell-specific barcodes in each cell, see U.S. application Ser. No. 13/981,711 filed on Apr. 15, 2016, the contents of which are hereby incorporated by reference in its entirety.

As used herein, the terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "amplification" refers to a process of making additional copies of the target nucleic acid. Amplification can have more than one cycle, e.g., multiple cycles of exponential amplification. Amplification may have only one cycle (making a single copy of the target nucleic acid). The copy may have additional sequences, e.g., those present in the primers used for amplification. Amplification may also produce copies of only one strand (linear amplification) or preferentially one strand (asymmetric PCR).

The term "sequencing" refers to any method of determining the sequence of nucleotides in the target nucleic acid.

The term "MHC" refers to the major histocompatibilty complex which is a quaternary peptide structure comprising a non-covalent complex of $\alpha 1$, $\alpha 2$ and $\alpha 3$ peptides and $\beta 2$ microglobulin peptides (for MHC-I) or a non-covalent complex of $\alpha 1$, $\alpha 2$, $\beta 1$ and $\beta 2$ peptides (for MHC-II). MHC bound to a peptide antigen is referred to as "pMHC."

The terms "TCRA and TCRB," "TCRalpha and TCRbeta," and "TCR$\alpha$ and TCR$\beta$" are used interchangeably to refer (depending on the context) to T-cell receptor alpha and beta peptide chains and genes coding therefor. See Thomas J. Kindt; Richard A. Goldsby; Barbara Anne Osborne; Janis Kuby (2007). *Kuby Immunology*. Macmillan.

The invention is a method of identifying an antigen for a T-cell receptor. More precisely, the invention is a method of identifying a pair of T-cell receptor-coding genes TCRA and TCRB forming a functional T-cell receptor consisting of TCRalpha and TCRbeta peptide chains and further identifying a sequence of a cognate antigen for the functional T-cell receptor. The invention relies on several innovative approaches: i. representative sampling of tumor tissue for massively parallel DNA sequencing; ii. utilization of molecular barcodes to tag all system components that are part of biologically relevant complexes; iii. preparation of high affinity, stable complex between a TCR and a peptide ligand; and iv. interrogation of the tagged system components using nucleic acid barcodes that can be read by massively parallel DNA sequencing.

As summarized in FIG. 1, the invention comprises the steps of (1) obtaining tumor tissue; (2) dissociating the tissue into cells or nuclei; (3) sorting of tumor, normal and immune cells; (4) obtaining tumor, normal and immune cell fractions; (5) isolating DNA from the cell fractions; (6) converting the tumor DNA into a sequencing library for tumor DNA sequencing; (7) preparing the paired TCRA and TCRB genes for sequencing; (8) DNA sequencing; (9) interpreting sequencing data; (10) forming a ranked list of genes encoding predicted immunogenic neoantigen peptides; and (11) forming a ranked list of T-cell receptor sequences (TCRA and TCRB) with observed or inferred TCRA/TCRB pairing.

Figure 2A:
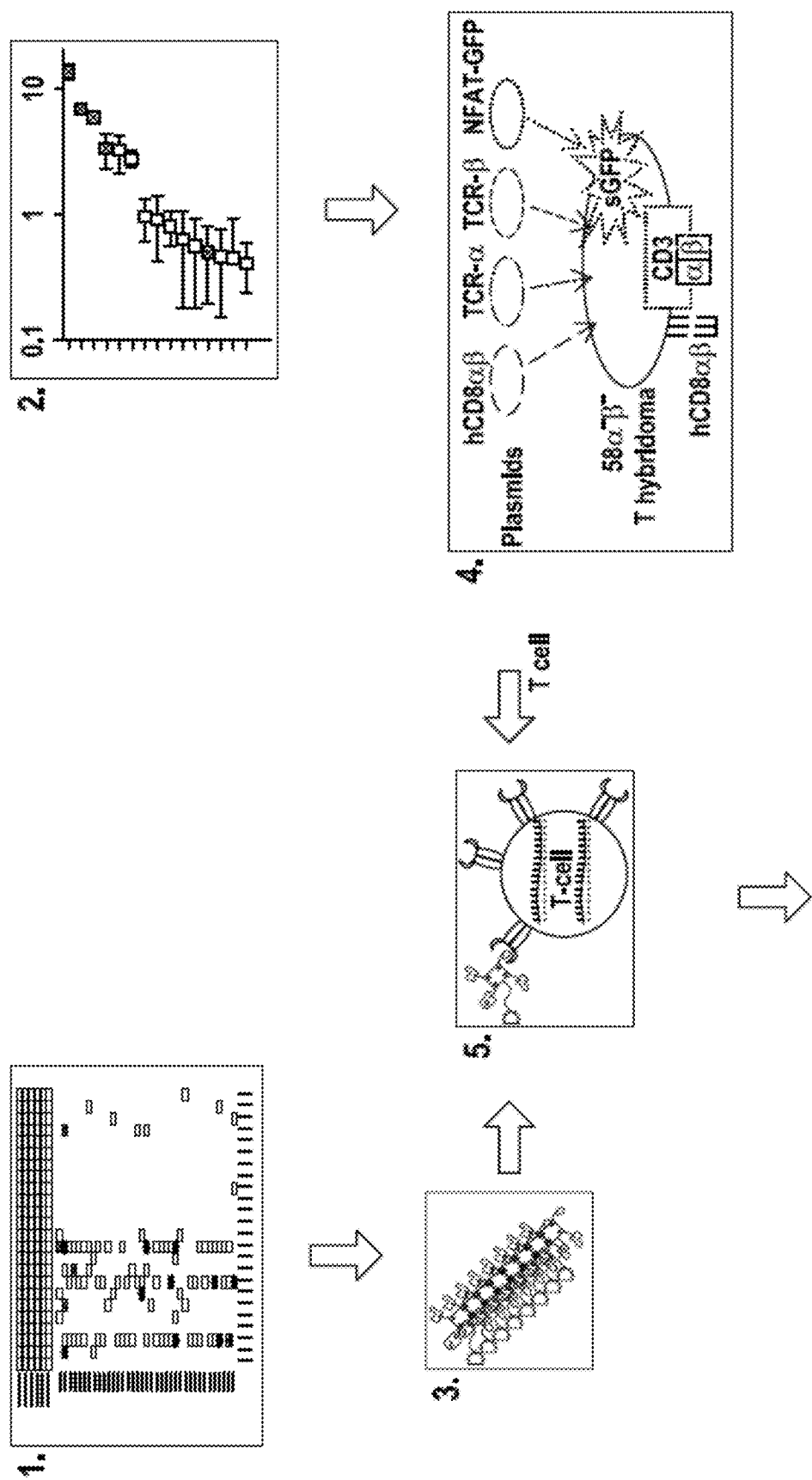
FIG. 2A and FIG. 2B shows a diagram of steps (steps 1-7) of the method from generating ranked lists of neoantigens and T-cell receptor sequences to resolving cognate TCR gene pairs and matching antigen peptides.
Figure 2B:
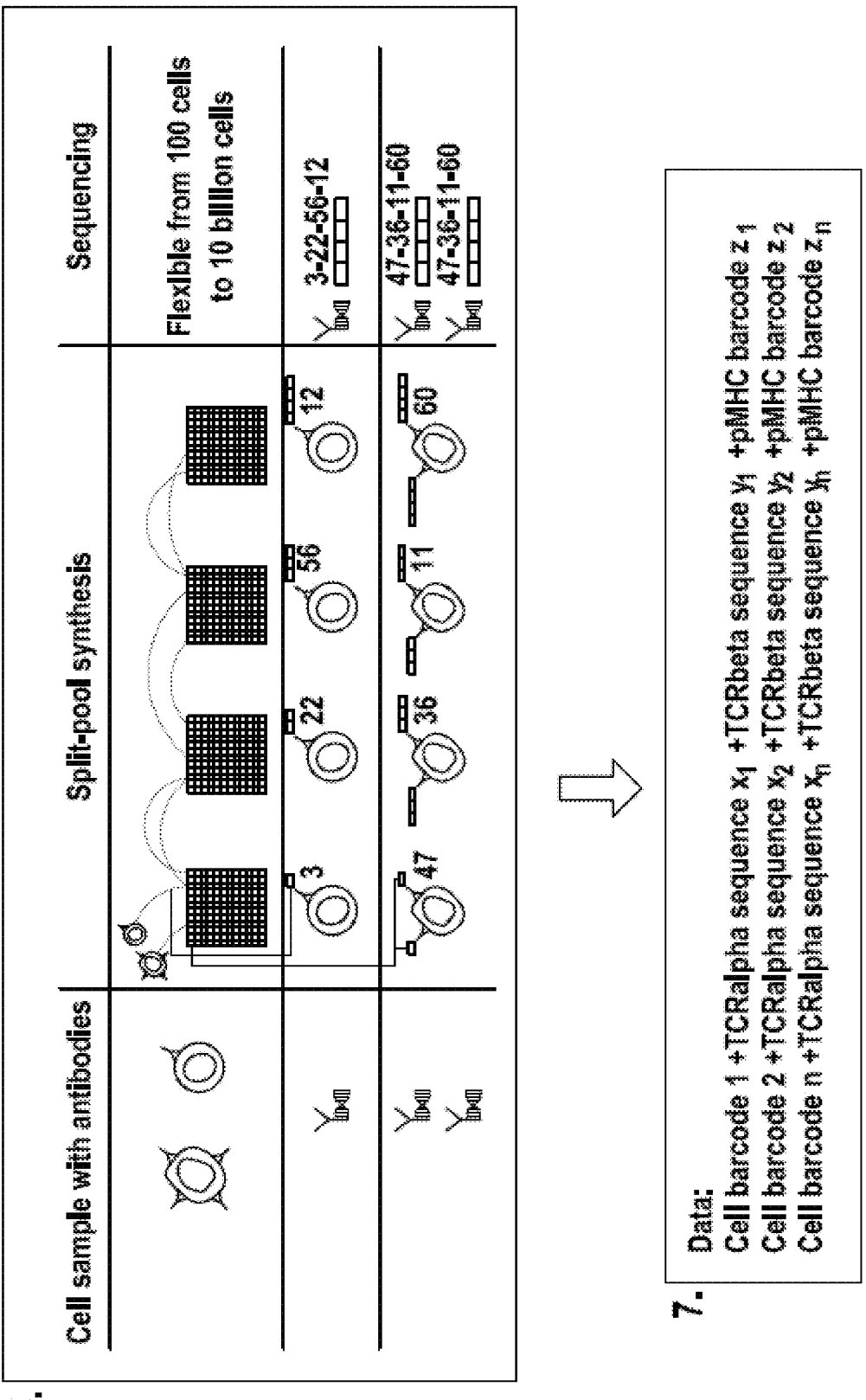

As summarized in FIG. 2A and FIG. 2B, starting with (1) the ranked list of genes encoding predicted immunogenic neoantigen peptides and (2) the ranked list of T-cell receptor sequences (TCRA and TCRB) with observed or inferred TCRA/TCRB pairing from FIG. 1, the invention further comprises the steps of (3) forming a library of DNA-barcoded neoantigen peptide-MHC complexes; (4) forming transgenic T cells expressing the identified and ranked TCR-A/B sequences, CD3 receptor and a CD8 co-receptor; (5) incubating the population of TCR-expressing transgenic T-cells with library of DNA-barcoded neoantigen peptide-MHC complexes; (6) subjecting the complex (5) to combinatorial barcoding and NGS sequencing of TCRA mRNA (plasmid), TCRB mRNA (plasmid) and a barcode from the DNA-barcoded peptide-MHC complexes; (7) sequencing the barcodes and the sequencing data interpretation, resolving cognate TCR pairs and matching peptides.

Referring to FIG. 1 step 1, a sample is derived from a subject or a patient. In some embodiments the sample may comprise a fragment of a solid tissue or a solid tumor derived from the subject or the patient, e.g., by biopsy or surgical resection. Referring to FIG. 1 step 2, the method comprises a step of dissociating the tumor to obtain a mixture or suspension of cells. Tumor tissue may be either fresh, flash frozen (e.g. in liquid nitrogen), or fixed using formalin, paraformaldehyde etc. Tumor tissue may be homogenized using a combination of mechanical dissociation (blending, e.g. using a homogenizer such as the Tube Mill, (IKA Works, Inc., Wilmington, N.C.)) and enzymatic digestion with proteolytic enzymes. In some embodiments, tissue disaggregation is exclusively enzymatic and employs one or more of trypsin, chymotrypsin, papain, collagenase, dispase (neutral protease), elastase, hyaluronidase, proteinase K and pronase.

A typical tumor sample is not homogeneous but contains a heterogeneous population of tumor cells as well as normal cells and immune cells. The immune cells in the tumor may comprise tumor infiltrating lymphocytes. Each type of cell in the sample is characterized by one or more biomarkers that can be used for cell separation e.g., via fluorescence activated cell sorting (FACS). Referring to FIG. 1 steps 3 and 4, the cells are separated into fractions. Tumor cells or nuclei may be characterized by tumor biomarkers including cytokeratins, p53, p63 proteins; or by DNA contents, since tumor cells are typically polyploid. In some embodiments, the cells are characterized by phospholipid or glycolipid content. Lymphocytes, depending on the type, are characterized by a set of surface proteins that alone or in combination, by presence or by absence serve as biomarkers for the type of lymphocytes. In some embodiments, T cells are distinguished by a combination of biomarkers $CD3^+CD8^+$ $TCR^+$. In some embodiments, naïve T cells are distinguished by a combination of biomarkers $CD45RA^+CD45RO^-$ $CCR7^+CD62L^+$. In some embodiments, central memory T cells are distinguished by a combination of biomarkers $CD45RA-CD45RO^+CCR7^+CD62L$. In some embodiments, effector memory T cells are distinguished by a combination of biomarkers $CD45RA-CD45RO^+CCR7^-CD62L^-$. In some embodiments, effector T-cells are distinguished by a combination of biomarkers $CD45RA^+CD45RO^-CCR7^-CD62L^-$. In some embodiments, regulatory T-cells are distinguished by a combination of biomarkers $CD4^+CD25^+$ $FoxP3^+$.

In some embodiments, the antigen sequences and the TCR sequences are determined by sequencing the nucleic acids isolated from fractionated cells (FIG. 1 step 5).

In some embodiments, the TCRA and TCRB sequences coding for peptides forming a functional TCR are identified using a method involving compartmentalization, PCR amplification and sequencing of TCR sequences to find TCRA and TCRB present in the same compartment, see e.g., Howie, B., et al., *High-throughput pairing of T cell receptor α and β sequences*. Science Translational Medicine, 2015. 7(301): p. 301ra131-301ra131 Briefly, T-cells are compartmentalized in individual compartments. Nucleic acids coding for TCR chains are obtained from genomic DNA or from total cellular RNA (converted into cDNA). The presence of multiple molecules of mRNA makes cDNA preferable to genomic DNA (gDNA). The TCRA and TCRB sequences are then PCR-amplified within each well.

In some embodiments, (see FIG. 1, step 7) the paired TCRA and TCBR genes are identified by a method comprising partitioning the population of T-cells into a plurality of first partitions containing a single cell; mixing the cell-containing partitions with a plurality of second partitions each containing multiple copies of barcoded oligonucleotide TCR primers comprising a TCR gene-binding sequence and a barcode, wherein the barcodes are the same within each partition but differ among partitions; fusing the first and second partitions; and copying the TCR genes with the barcoded TCR primers thereby forming barcoded TCR gene amplicons, and sequencing the barcoded TCR amplicons to determine which TCRA and TCRB amplicons have the same barcode indicating co-occurrence in one cell. (FIG. 1, step 8).

In some embodiments, the paired TCRA and TCBR genes are identified by a method comprising sequencing and combinatorial analysis, see e.g., Howie, B et al., "High-throughput pairing of T cell receptor α and β sequences." Science translational medicine 7, no. 301 (2015): 301ra131-301ra131. Briefly, the method comprises partitioning the population of T-cells into a plurality of partitions containing groups of cells; ligating barcoded adaptors to nucleic acids in each partition; sequencing the TCRA and TCRB in the adapted nucleic acids to obtain barcoded TCRA and TCRB sequences; determining TCRA and TCRB gene pairs base on frequency of co-occurrence in partitions. In some embodiments, CDR3 region within the TCR genes is targeted e.g., with primers specific for the V and C gene segments or any segments present in the CDR3 region. In some embodiments, the sequencing is accomplished by pooling the barcoded amplicons for high-throughput DNA sequencing, which reads both the receptor sequence and the barcode for each strand. The sequenced barcodes allow mapping of the receptor sequences to the wells of origin. In some embodiments, TCRA and TCRB matching employs statistical analysis. Statistical analysis is used to compare the well occupancy pattern of every TCRA sequence against that of every TCRB sequence; sequences that share more wells than expected by chance are marked as possible pairing partners. Additional statistical methods are used to identify the TCRA and TCRB pairs encoding a functional TCR, e.g., a method comprising generating a null distribution by permutation and identifying the pairs that satisfy a target false discovery rate. See US20100330571, the contents of which are hereby incorporated by reference in its entirety.

In some embodiments, the TCRA and TCRB sequences coding for peptides forming a functional TCR are identified from individual T-cells. The T-cells may be cloned and the TCR genes sequenced, e.g., by a method involving hybrid capture and sequencing see Linnemann, C., et al., *High-throughput identification of antigen-specific TCRs by TCR gene capture*. Nat Med, 2013. 19(11): p. 1534-154. Briefly, in one example, a bait library is used to target each individual variable (V) and joining (J) element within the TCRA and TCRB loci at 8 and 6 baits per locus respectively. The baits capture TCR-coding sequences from genomic DNA. The captured sequences are sequenced by a method comprising ligation of barcoded adaptors and paired-end deep sequencing. The sequence data is analyzed to reconstruct TCR J genes, TCRB D genes and TCR V genes. CDR3 region sequence is determined as the nucleotide sequence between the conserved TCR V cysteine and TCR J phenylalanine residues. In other embodiments, the individual T-cells are encapsulated in vessels (e.g., water in oil emulsion) with vessel-specific barcodes (e.g., oligonucleotides that serve as reverse-transcription (RT) primers for reverse transcription of TCR genes' mRNA). See e.g., application Ser. No. WO2016176322.

In some embodiments, the invention comprises forming a ranked list of ranked T-cell receptor sequences, each comprising a pair of TCRA and TCRB genes encoding TCRalpha and TCRbeta chains. (FIG. 1, steps 9 and 11.)

In some embodiments, the invention comprises a step of forming a T-cell expressing an engineered TCR. (FIG. 2A, step 4). The cell preferably is a T-cell that does not produce an endogenous TCR as explained in detail in subsequent sections. Several methods are known in the art to produce a T-cell expressing a Chimeric Antigen Receptor (CAR), see e.g., Essand, M. and A. S. Loskog, *Genetically engineered T cells for the treatment of cancer*. J Intern Med, 2013. 273(2): p. 166-81). In some embodiments, viral vectors are used to introduce the TCRA and TCRB genes, e.g., retroviral vectors where the genes encode the TCR-alpha and TCR-beta chains fused with a picornavirus 2A self-cleaving peptide linker, see e.g., Zhang, Y., et al., *Transduction of Human T Cells with a Novel T-Cell Receptor Confers Anti-HCV Reactivity*. PLOS Pathogens, 2010.6(7): p. e1001018 and Walchli, S., et al., *A practical approach to T-cell receptor cloning and expression*. PLoS One, 2011. 6(11): p. e27930. In some embodiments, elements are introduced to enhance the formation of engineered TCR. The enhancements include using murine constant TCR domains to enhance TCR expression, adding zipper domains to the intracellular TCR domains to promote interchain recognition and binding, or engineering disulfide bonds in the extracellular part of the constant domain to increase interchain affinity, see e.g., U.S. Pat. No. 9,624,292 B2 and Kuball, J., et al., *Facilitating matched pairing and expression of TCR chains introduced into human T cells*. Blood, 2007. 109(6): p. 2331. Additional enhancements include co-transfection of target cells with an MSCV vector with cloned human CD3 complex, in order to improve cell surface expression levels of TCR, see e.g., Guo, X.-z. J., et al., *Rapid cloning, expression, and functional characterization of paired αβ and γδ T-cell receptor chains from single-cell analysis*. Molecular Therapy. Methods & Clinical Development, 2016. 3: p. 15054.

In some embodiments, expression vectors are not used but the TCRA and TCRB gene pairs are introduced into cells as transcriptionally active DNA fragments such as PCR amplicons. In some embodiments, reagents facilitating transfection are used, e.g., TransIT-293 reagent (Mirus Bio, Madison, Wis.) In yet other embodiments, the TCRA and TCRB gene pairs are introduced into cells as functional mRNA, e.g., in vitro transcribed mRNA. See e.g., Simon, P., et al., *Functional TCR Retrieval from Single Antigen-Specific Human T Cells Reveals Multiple Novel Epitopes*. Cancer Immunol Res, 2014. 2(12): p. 1230-1244 where the mRNA was produced by T7 polymerase and comprised 3' modifications for increased RNA stability and translational efficiency, such as 3' UTR of human β-globin gene.

In some embodiments, the TCRA and TCRB gene pairs are introduced into a receptive T-cell. (FIG. 2A, step 5). In some embodiments, the T-cell is lacking endogenous TCR genes, see e.g., Zhang, Y., et al., *Transduction of Human T Cells with a Novel T-Cell Receptor Confers Anti-HCV Reactivity*. PLOS Pathogens, 2010. 6(7): p. e1001018 and Simon, P., et al., *Functional TCR Retrieval from Single Antigen- Specific Human T Cells Reveals Multiple Novel Epitopes*. Cancer Immunol Res, 2014. 2(12): p. 1230-1244, examples of TCRA/B negative Jurkat76 cell line. In other embodiments, the cell is a T-cell hybridoma, se e.g., Siewert, K., et al., *Unbiased identification of target antigens of CD8+T cells with combinatorial libraries coding for short peptides*. Nat Med, 2012. 18(5): p. 824-8. In some embodiments, the T-cell is further engineered to express the CD4 co-receptor. In some embodiments, the T-cell can be further engineered to express a reporter gene (e.g. a fluorescent protein such as GFP or luciferase) upon TCR-antigen recognition and subsequent T-cell activation. The reporter construct can comprise a responsive promoter such as an NFAT protein-responsive promoter upregulated upon T-cell activation.

In some embodiments, the invention comprises a step of making and sequencing a library of sequencing-ready target nucleic acids. The target nucleic acids may comprise the TCRA and TCRB genes obtained from the sample. The target nucleic acids may also be the tumor exome comprising coding sequences for tumor neoantigens (tumor exome). As described herein, the library comprises individual molecules with additional features including but not limited to adaptors, barcodes and primer binding sites. The target sequences are conjugated (e.g., by ligation or by primer extension) to said additional features.

In some embodiments, sequencing the nucleic acid isolated from the tumor material involves a step of library preparation. (FIG. 1, step 6.) The step comprises forming adapted nucleic acids wherein adaptor molecules are ligated to the target nucleic acid to enable barcoding and sequencing. The ligation can be a blunt-end ligation or a more efficient cohesive-end ligation. The target nucleic acid or the adaptors may be rendered blunt-ended by "end repair" comprising strand-filling, i.e., extending a 3'-terminus by a DNA polymerase to eliminate a 5'-overhang. In some embodiments, the blunt-ended adaptors and target nucleic acid may be rendered cohesive by addition of a single nucleotide to the 3'-end of the adaptor and a single complementary nucleotide to the 3'-ends of the target nucleic acid, e.g., by a DNA polymerase or a terminal transferase. In yet other embodiments, the adaptors and the target nucleic acid may acquire cohesive ends (overhangs) by digestion with restriction endonucleases. The latter option is more advantageous for known target sequences that are known to contain the restriction enzyme recognition site. In some embodiments, other enzymatic steps may be required to accomplish the ligation. In some embodiments, a polynucleotide kinase may be used to add 5'-phosphates to the target nucleic acid molecules and adaptor molecules.

In embodiments where adaptors are added independently of the sequence of the target nucleic acid, for example, by ligation the target nucleic acids in the sample receive the same adaptor molecule at each end. To distinguish the strands of the resulting adapted target nucleic acid, the adaptor may have a Y-structure, see e.g., U.S. Pat. Nos. 8,053,192, 8,182,989 and 8,822,150.

In some embodiments, adaptors comprise a primer binding site, e.g., an amplification primer binding site or a sequencing primer binding site. In some embodiments, the adaptor molecules are in vitro synthesized artificial sequences. In other embodiments, the adaptor molecules are in vitro synthesized naturally-occurring sequences. In yet other embodiments, the adaptor molecules are isolated naturally occurring molecules.

In some embodiments, the invention is a method comprising a step of amplifying the target nucleic acid. The amplification may be by exponential polymerase chain reaction (PCR), linear amplification of only one strand or any other method that utilizes oligonucleotide primers. Various PCR conditions are described in *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, N Y, 1990).

In some embodiments, amplification utilizes a universal primer binding site present in the adaptor that is conjugated to the target sequence as set forth above. In other embodiments, a gene-specific (target-specific) primer or primer pair is used. In some embodiments, primers contain a 5'-overhang comprising adaptor sequences, e.g., barcodes or sequencing primer binding sites. The use of such primers dispenses with the adaptor ligation step in the method of the instant invention.

In some embodiments, the invention comprises introduction of barcodes into the target nucleic acids especially for sequencing. Sequencing individual molecules typically requires molecular barcodes such as described e.g., in U.S. Pat. Nos. 7,393,665, 8,168,385, 8,481,292, 8,685,678, and 8,722,368 as well as 7,264,929, the contents of which are hereby incorporated by reference in their entireties. A unique molecular barcode is a short artificial sequence added to each molecule in a sample such as a patient's sample typically during the earliest steps of in vitro manipulations. The barcode marks the molecule and its progeny. The unique molecular barcode (UID) has multiple uses. Barcodes allow tracking each individual nucleic acid molecule in the sample to assess, e.g., the presence and amount of circulating tumor DNA (ctDNA) molecules in a patient's blood in order to detect and monitor cancer without a biopsy. See U.S. patent publication no. US 2016/0032396A1, the contents of which are hereby incorporated by reference in its entirety. Unique molecular barcodes can also be used for sequencing error correction. The entire progeny of a single target molecule is marked with the same barcode and forms a barcoded family. A variation in the sequence not shared by all members of the barcoded family is discarded as an artifact and not a true mutation. Barcodes can also be used for positional deduplication and target quantification, as the entire family represents a single molecule in the original sample. See Id.

In some embodiments of the present invention, adaptors comprise one or more barcodes. A barcode can be a multiplex sample ID (MID) used to identify the source of the sample where samples are mixed (multiplexed). The barcode may also serve as a UID used to identify each original molecule and its progeny. The barcode may also be a combination of a UID and an MID. In some embodiments, a single barcode is used as both UID and MID. In some embodiments, each barcode comprises a predefined sequence. In other embodiments, the barcode comprises a random sequence. Barcodes can be 1-20 nucleotides long.

Sequencing can be performed by any method known in the art. Especially advantageous is the high-throughput single molecule sequencing capable of reading circular target nucleic acids. Examples of such technologies include the SOLiD platform (ThermoFisher Scientific, Foster City, Calif.), Heliscope fluorescence-based sequencing instrument (Helicos Biosciences, Cambridge, Mass.) Pacific BioSciences platform utilizing the SMRT (Pacific Biosciences, Menlo Park, Calif.) or a platform utilizing nanopore technology such as those manufactured by Oxford Nanopore Technologies (Oxford, UK) or Roche Sequencing Solutions (Roche Genia, Santa Clara, Calif.), via a reversible terminator Sequencing by Synthesis (SBS) (Illumina, San Diego, Calif.) and any other presently existing or future DNA sequencing technology that does or does not involve sequencing by synthesis. The sequencing step may utilize platform-specific sequencing primers. Binding sites for these primers may be introduced in the method of the invention as described herein, i.e., by being a part of second adaptors or amplification primers.

Analysis and Error Correction

In some embodiments, the sequencing step involves sequence analysis including a step of sequence aligning. In some embodiments, aligning is used to determine a consensus sequence from a plurality of sequences, e.g., a plurality having the same barcodes (UID). In some embodiments barcodes (UIDs) are used to determine a consensus from a plurality of sequences all having an identical barcode (UID). In other embodiments, barcodes (UIDs) are used to eliminate artifacts, i.e., variations existing in some but not all sequences having an identical barcode (UID). Such artifacts resulting from PCR errors or sequencing errors can be eliminated.

In some embodiments, the number of each sequence in the sample can be quantified by quantifying relative numbers of sequences with each barcode (UID) in the sample. Each UID represents a single molecule in the original sample and counting different UIDs associated with each sequence variant can determine the fraction of each sequence in the original sample. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

The invention further comprises a step of identifying tumor neoantigens. In some embodiments, the method comprises a step of sequencing the tumor-associated genetic material by whole genome sequencing (WGS), whole exome sequencing (WES) or more selective sequencing of genetic material enriched for tumor associated expressed genes. (FIG. 1, steps 5, 6 and 8). The method further comprises alignment to a reference genome. Thereby the neoantigens are identified as sequences comprising differences (mutations) in coding sequences when compared to a reference genome. Only the missense mutations (i.e., the mutations altering the amino acid coding) are scored as potentially neoantigenic mutations.

In some embodiments, neoantigens are discovered by serum antibody screening using peptide arrays. In this embodiment, an addressable array of up to 2.5 million peptides between 8 and 20 amino acids-long is synthesized as described in U.S. Pat. No. 9,346,892, the contents of which are hereby incorporated by reference in its entirety. The array is screened with serum from tumor patients and antibody binding is detected by a colorimetric or fluorescent assay, e.g., ELISA assay. The array peptides identified as having immune response (antibody binding) are selected as neoantigens.

In some embodiments, the step of identifying neoantigens further comprises a step of tentative neoepitope prediction or a step of tentative antigenic peptide prediction as described e.g., in Kvistborg, P., et al., *Immune monitoring technology primer: whole exome sequencing for neoantigen discovery and precision oncology*. Journal for ImmunoTherapy of Cancer, 2016. 4(1): p. 22. Tran, E., P. F. Robbins, and S. A. Rosenberg, '*Final common pathway' of human cancer immunotherapy: targeting random somatic mutations*. Nat Immunol, 2017. 18(3): p. 255-262, Anagnostou, V., et al., *Evolution of Neoantigen Landscape During Immune Checkpoint Blockade in Non-Small Cell Lung Cancer*. Cancer Discov, 2016, Zolkind, P., et al., *Neoantigens in immunotherapy and personalized vaccines: Implications for head and neck squamous cell carcinoma*. Oral Oncology., Kreiter, S., et al., *Mutant MHC class II epitopes drive therapeutic immune responses to cancer*. Nature, 2015. 520(7549): p. 692-6, Hegde, P. S., V. Karanikas, and S. Evers, *The Where, the When, and the How of Immune Monitoring for Cancer Immunotherapies in the Era of Checkpoint Inhibition*. Clin Cancer Res, 2016. 22(8): p. 1865-74, Yuan, J., et al., *Novel technologies and emerging biomarkers for personalized cancer immunotherapy*. J Immunother Cancer, 2016. 4: p. 3. For example, a mutant peptide is identified as a neoantigen if one or more of the following favorable characteristics are found: the mutation is known to be associated with tumors e.g., is present in the COSMIC database (a database containing a comprehensive list of somatic mutations found in human cancers), the mutated peptide is 8-15 amino acids in length, the mutated peptide sequence is located within the protein near a sequence promoting proteasome cleavage, the mutated peptide sequence is located within the protein near a recognition site for Transporter associated with Antigen Processing (TAP).

In some embodiments, the invention further comprises a step of predicting the level of binding of the neoantigen to an MHC allele. In some embodiments, the level of binding is determined by a sequence based in silico assessment (e.g., the prediction is made using one or more of Hidden Markov models, machine learning algorithm, and neural networks. In other embodiments, the level of binding is determined by a structure based in silico assessment, for example using known peptide antigen-MHC crystal structures, a prediction can be made whether a given peptide will bind to the MHC molecule, see Sharma, G. and R. A. Holt, *T-cell epitope discovery technologies*. Human Immunology, 2014. 75(6):

p. 514-519. In yet other embodiments, level of binding is determined experimentally wherein the measured affinity of the peptide to MHC is less than 1 micromole, e.g., 500 nM, 200 nM or as low as 50 nM or less.

In some embodiments, the method comprises a step of generating a ranked list of tumor-derived neoantigen sequences. (FIG. 1, steps 9 and 10).

The invention further comprises a step of forming the candidate neoantigenic peptides and coupling them with MHC molecules to form an antigen presenting complex (FIG. 2A, step 3). In some embodiments, the peptides are formed using existing in vitro peptide synthesis methods, e.g., those described in Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984), the contents of which are hereby incorporated by reference in their entireties. The peptides may also be synthesized using a microarray wherein amino acids are introduced with an amino group Reply to Non-Final Office Action, dated Jul. 26, 2022 protected by a photolabile protective group as described in U.S. Pat. No. 9,346,892, the contents of which are hereby incorporated by reference in its entirety.

The invention further comprises a step of forming an antigen-presenting polypeptide complex. The complex is the MHC-I complex comprising a non-covalent complex of $\alpha 1$, $\alpha 2$ and $\alpha 3$ peptides and $\beta 2$ microglobulin peptides or the MHC-II complex comprising a non-covalent complex of $\alpha 1$, $\alpha 2$, $\beta 1$ and $\beta 2$ peptides. In some embodiments, the MHC peptides are patient-specific. The patient-specific protein sequences are obtained by determining the nucleic acid sequence of one or more of the patient's Class Ia and Class Ib gene sequences including one or more of HLA-A, HLA-B, HLA-C, HLA-E, HLA-F and HLA-G loci. In some embodiments, expression vectors for producing the MHC peptides are formed from the patient's HLA gene sequences. In some embodiments, the patient's HLA gene sequences are determined by low resolution typing of HLA-A and HLA-B genes and ranking the sequences to determine the most likely alleles, see e.g., Emerson, R., et al. *Immunosequencing identifies signatures of cytomegalovirus exposure history and HLA-mediated effects on the T cell repertoire*. Nature Genetics 49, no. 5 (2017): 659.

In some embodiments, multimers of MHC complexes are used. In some embodiments, the MHC multimers are dimers, tetramers or octamers. In some embodiments, MHC multimers are produced by capturing multiple MHC monomers on a backbone molecule. In some embodiments, the backbone is a polymer molecule such as dextran or another carbohydrate polymer. In some embodiments, the backbone contains an affinity capture molecule. In some embodiments, MHC multimers are formed by capturing recombinantly produced biotinylated MHC monomers on a streptavidin or avidin bound to dextran. In some embodiments, the multimers are tetramers.

In some embodiments, MHC multimers are conjugated to a detection molecule. In some embodiments, the detection molecule is a fluorochrome conjugated to the backbone to enable isolation of T-cells bound to the MHC multimers via flow cytometry. In some embodiments, the detection molecule is a heavy metal conjugated to the backbone (e.g., by method described in Newell, E. W. et al., (2012). *Cytometry by time-of-flight shows combinatorial cytokine expression and virus-specific cell niches within a continuum of CD8+ T cell phenotypes*. Immunity, 36(1), 142-152)) to enable detection by mass cytometry. See Sharma, G. and R. A. Holt, T-cell epitope discovery technologies. Human Immunology, 2014. 75(6): p. 514-519; Altman, J. D. and M. M. Davis, *MHC-Peptide Tetramers to Visualize Antigen-Specific T Cells*. Curr Protoc Immunol, 2016. 115: p. 17 3 1-17 3 44.

The invention further comprises barcoding the MHC multimers. In some embodiments, the barcode is a single stranded or a double stranded nucleic acid molecule. The barcode nucleic acid molecule may be captured to the same backbone as the MHC multimers. In one example, the barcode is a biotinylated DNA molecule which is captured on the same dextran modified with streptavidin or avidin to which the MHC molecules are bound. See Bentzen, A. K., et al., *Large-scale detection of antigen-specific T cells using peptide-MHC-I multimers labeled with DNA barcodes*. Nat Biotechnol, 2016. 34(10): p. 1037-1045. In some embodiments, the nucleic acid barcode is 10, 15, 20 or 25 bases or base pairs long. The barcoding has the potential of labeling as many as $\sim 10^{10}$ different MHC multimers. In some embodiments, the MHC multimers used to capture cells are conjugated to an oligonucleotide probe. After the cells capture, a nucleic acid probe complementary to a region of the conjugated oligonucleotide is hybridized to each pMHC multimer bound to each cell.

The invention further comprises a step of capturing T-cells bound to MHC multimers. In some embodiments the cells are stained with barcoded p-MHC multimers and co-stained with mAbs using standard immunology protocols. For instance, human T cells are incubated with Fc blocker and then with p-MHC multimers prior to the QBC procedure.

The invention further comprises a step of barcoding T-cells. In one aspect, the T-cells are barcoded to identify the TCRA and TCRB genes found in the same T-cell (and thus forming a functional TCR). In another aspect, the T-cells are barcoded to identify each cell bound to a barcoded MHC multimer.

In some embodiments, the cell barcoding is Quantum Barcoding (QBC) method described e.g., in U.S. patent application Ser. No. 13/981,711 filed on Apr. 15, 2016. Briefly, a plurality of cells in a mixture is subjected to a following process: the cells are contacted with a mixture of oligonucleotide specific for intracellular nucleic acid targets. The oligonucleotide has a gene-binding sequence and a barcode oligonucleotide annealing region, the cells are further contacted with barcode oligonucleotides complementary to the barcode oligonucleotide annealing region in the TCR primer; the cells are further contacted with additional barcode oligonucleotides in each of one or more rounds of split pool synthesis wherein the barcoded oligonucleotide in each round comprises an annealing region complementary to the annealing region of the barcode oligonucleotide from the previous round, thereby assembling cell-specific barcodes on each TCR primer in each of the plurality of T-cells.

The probe targets can be RNA transcripts or DNA sequences. In the first round of barcoding aimed at identifying the TCR genes, the probes may be specific for the TCR genes. In the second round of barcoding aimed at identifying cells bound to MHC, the probes may be specific for any intracellular target i.e., selected from T-cell marker transcripts (TCRA, TCRB, CD3, CD4, CD8, FoxP3 etc.), the transcripts originating from either genomic or transfected DNA sequences.

The invention further comprises a step of obtaining sequencing data from each antigen-bound T-cell in order to match the T-cell receptor to its cognate antigen. (FIG. 2B, step 7). This step comprises determining in each cell, the sequence of the TCRA and TCRB gene, the sequence of the unique cellular barcode (for example, obtained via QBC) and the sequence of the barcode associated with the MHC multimer bound to the T-cell. As shown in FIG. 2A and FIG. 2B, and in more detail in FIG. 3, the match allows identifying the antigen to which the TCR is bound according to the following scheme:

(Cell barcode 1+TCRA sequence $x_1$)+(Cell barcode 1+TCRB sequence $y_1$)+(Cell barcode 1+pMHC barcode $z_1$)

(Cell barcode 2+TCRA sequence $x_2$)+(Cell barcode 2+TCRB sequence $y_2$)+(Cell barcode 2+pMHC barcode $z_2$)

(Cell barcode n+TCRA sequence $x_n$)+(Cell barcode n+TCRB sequence $y_n$)+(Cell barcode n+pMHC barcode $z_n$).

EXAMPLES

Example 1 (Prophetic)

In this example, a fragment of a surgically resected tumor is obtained. The tumor sample is dissociated into single cells using a combination of mechanical and enzymatic tissue dissociation methods. The dissociated cells are sorted by fluorescence-activated cell sorting (FACS) into tumor cells, normal tissue cells and immune cells (tumor infiltrating lymphocytes (TILs)) using surface, intracellular or nuclear markers specific for each cell type. The tumor cell biomarker is cytokeratin while the T-cell combination of biomarkers is $CD3^+CD8^+TCR^+$. The nucleic acids are isolated from the separate fractions of tumor cells, normal cells and T-cells and optionally quantified using KAPA Express Extract kit and KAPA HiFi QC reagents (Kapa Biosystems, Wilmington, Mass.).

The nucleic acids from tumor and normal (non-lymphocyte) cells are subjected to sequencing library preparation using KAPA Hyper Prep Kit and exome sequence capture using the SeqCap® EZ Human Exome Probes v3.0 (Roche Sequencing Solutions, Madison, Wis.). The captured library nucleic acids are sequenced on any Illumina instrument (MiSeq®, NextSeq, HiSeq® or NovaSeq®) according to the manufacturers' recommendations.

The sequence data is compared via a sequence alignment algorithm to identify non-synonymous substitutions in the coding regions as potential neoantigens. The potential neoantigens are evaluated in silico for their ability to bind the MHC-I complex of the patient. The evaluation produces a ranked list of antigenic neoantigens. The peptides predicted to bind to MHC with high affinity are used to construct a neoantigen library. The peptides are synthesized in vitro using the array method described in U.S. Pat. No. 9,346,892, the contents of which are hereby incorporated by reference in its entirety.

MHC molecules comprising the alpha 1 chain, alpha 2 chain, and beta 2 microglobulin are formed by combining biotinylated peptide chains with streptavidin containing dextran backbone. The complexes are contacted with biotinylated DNA barcodes to form DNA-barcoded MHC tetramers. The barcoded MHC tetramers are combined with the antigenic peptides to form barcoded antigen-presenting complexes (APC). The peptides are used to form a library of DNA-barcoded peptide-MHC complexes.

Sequences of the barcoded TCRA and TCRB genes are matched by barcodes and analyzed for frequency of occurrence to form a ranked list of infiltrating tumor lymphocyte T-cell receptor sequences with observed or inferred alpha/beta pairing, inferred HLA type of a patient. The selected TCRA and TCRB genes in an expression plasmid are cotransfected with a plasmid expressing human CD8 alpha and beta subunits and with a GFP reporter plasmid into a Jurkat cell line. The population of TCR-specific transgenic T-cells incubated with the library of DNA-barcoded peptide-MHC complexes for antigen-TCR binding. The cells are stained with barcoded p-MHC multimers and co-stained with mAbs using standard immunology protocols. The additional antibodies may be targeted to cell type identifying markers e.g., CD4 or CD8, etc. For instance, human T cells are incubated in staining buffer (phosphate buffered saline PBS with 0.5% BSA) with Fc blocker for 30 min at 0° C. Cells are then washed in staining buffer and incubated for 30 min to 1 hr at 0° C. or room temperature with empirically determined concentrations of p-MHC multimers and/or antibodies. After staining, cells are washed several times in staining buffer and reconstituted at desired concentration in PBS for the downstream combinatorial barcoding (quantum barcoding or QBC) procedure.

Figure 3:
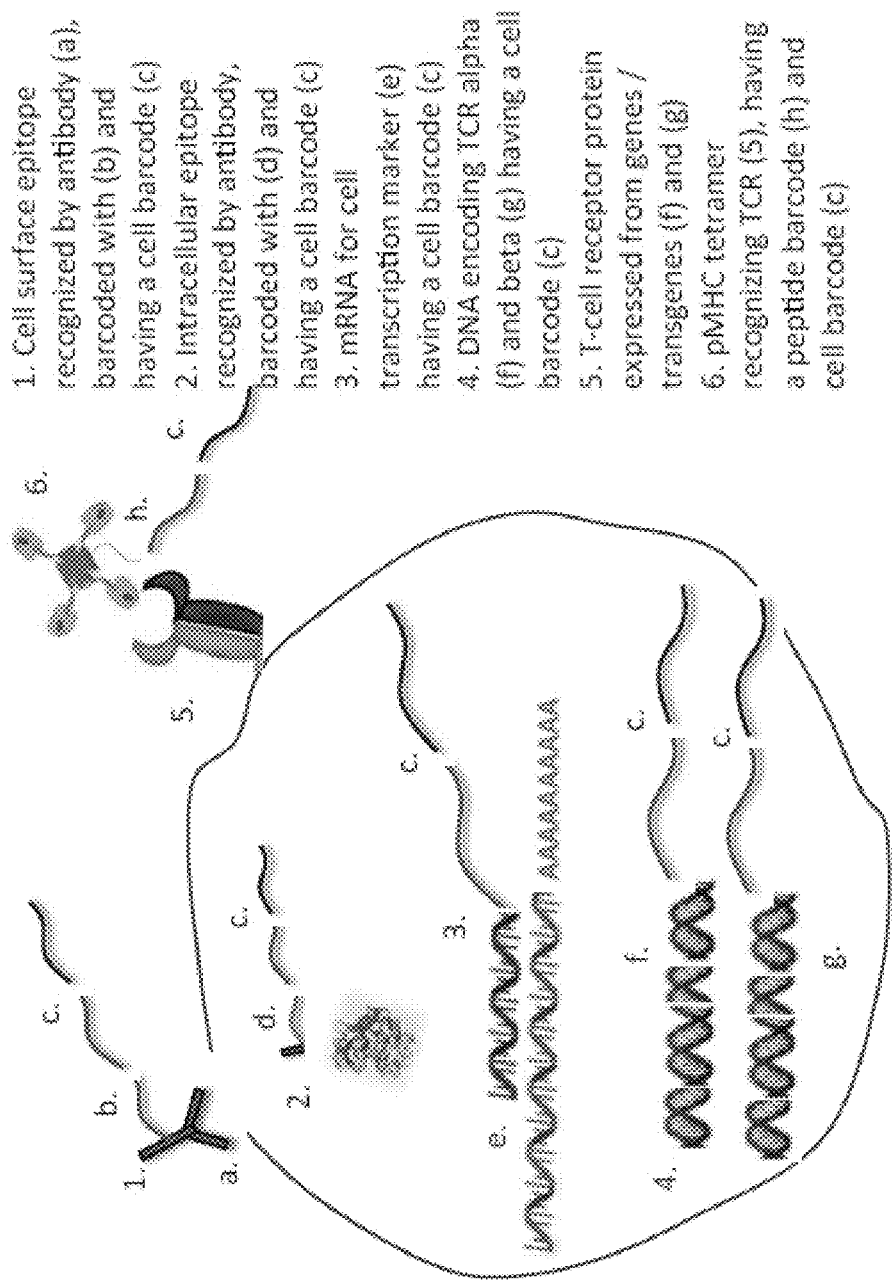
FIG. 3 illustrates the use of barcodes to match the T-cell receptor to its cognate antigen in the T-cell.

The cells bound to the peptide-MHC complexes undergo the process of combinatorial barcoding (QBC), wherein the TCRA mRNA, the TCRB mRNA and the p-MHC bound to the T-cell receptor expressed on the cell surface, are labeled with the same cell-specific barcode (FIG. 3). As illustrated on FIG. 3, (1) a cell surface epitope (a) can be recognized with an antibody barcoded with a target-specific nucleic acid barcode (b) and further barcoded with the cell-specific nucleic acid barcode (c). An intracellular epitope (2) can be recognized with an antibody barcoded with a target-specific nucleic acid barcode (d) and further barcoded with the same cell-specific nucleic acid barcode (c). Any nucleic acid target in the cell (3) has the sequence (e) and can be barcoded with the same cell-specific nucleic acid barcode (c). Examples of these sequences include a cell characterizing biomarker, e.g., TCRA, TCRB, CD3, CD4, CD8 and FoxP3. The TCR genes (4) TCRA (f) and TCRB (g) can be barcoded with the same cell-specific nucleic acid barcode (c). The TCRA (f) and TCRB (g) genes code for the peptides assembled in to a TCR (5) bound to an MHC-peptide multimer (6) having the peptide-associated nucleic acid barcode (h) the same cell-specific nucleic acid barcode (c).

The QBC procedure is a method comprising assembly of DNA barcodes attached to a target-specific nucleic acid such as barcode attached to an antibody or directly to a nucleic acid target. The DNA barcodes are assembled via several rounds of split pool synthesis wherein the barcoded oligonucleotide added in each round and the oligonucleotide comprises an annealing region complementary to the annealing region of the barcode oligonucleotides from the previous round, thereby assembling cell-specific barcodes on each primer (see U.S. application Ser. No. 13/981,711 filed on Apr. 15, 2016).

In the final step, the barcoded TCRA mRNA, the barcoded TCRB mRNA and the DNA barcodes from the peptide-MHC complexes are sequenced. The data is interpreted resolving cognate TCR gene pairs and matching peptide as having the same cellular barcode.

The invention claimed is:

1. A method of identifying a cognate antigen for a T-cell receptor (TCR) composed of an alpha chain (TCRα) and a beta chain (TCRβ), the method comprising:
   (a) obtaining a population of T-cells from a patient wherein each T-cell comprises a TCR comprising TCRα and TCRβ chains;
   (b) barcoding nucleic acids from each T-cell with a cell-specific barcode;
   (c) sequencing the barcoded nucleic acids to obtain TCRA and TCRB gene sequences coding for the TCRα and TCRβ chains;

(d) identifying TCRA and TCRB genes having the same barcodes as gene pairs encoding a functional TCR;

(e) introducing the TCRA and TCRB gene pairs identified in step (d) into a T-cell, by means of expression vectors, transcriptionally active DNA fragments, or mRNA;

(f) obtaining a population of tumor cells from the patient each possibly comprising one or more tumor neoantigen;

(g) identifying tumor neoantigen genes;

(h) synthesizing neoantigen peptides from the tumor neoantigen genes identified in step (g), by transcribing and translating the tumor neoantigen genes;

(i) combining the neoantigen peptides from step (h) with an MHC-1 antigen presenting complex and a barcode to form a barcoded MHC-neoantigen peptide complex;

(j) contacting the T-cells from step (e) with the barcoded MHC-neoantigen peptide complexes from step (i) to form cell-bound MHC-neoantigen-TCR complexes;

(k) further barcoding the TCR genes and the barcoded MHC-neoantigen peptide complex from each of the cell-bound MHC-neoantigen-TCR complexes formed from step (j) with a cell-specific barcode;

(l) sequencing the TCR genes associated with the cell-specific barcodes and sequencing the MHC-neoantigen complex barcodes associated with the cell-specific barcodes in the T-cells from step (k); and (m) identifying the neoantigen as the cognate antigen for the TCR if at least one of the TCR genes and MHC-neoantigen complex barcode are associated with the same cell-specific barcode.

2. The method of claim 1, wherein the population of T-cells is obtained by dissociation of tumor tissue.

3. The method of claim 1, wherein the TCRA and TCRB gene sequences coding for the TCRα and TCRβ chains are selected from rearranged DNA sequences or RNA sequences.

4. The method of claim 2, wherein the population of T-cells is obtained from the tumor by protein marker expression based capture.

5. The method of claim 1, wherein the T-cell barcoding in one or both steps (b) and (k) is performed by a method comprising:
(a) contacting the plurality of T-cells with a mixture of primers comprising a gene-specific sequence and a barcode oligonucleotide annealing region;
(b) contacting the plurality of T-cells with barcode oligonucleotides complementary to the barcode oligonucleotide annealing region in the primer; and
(c) contacting the plurality of T-cells with additional barcode oligonucleotides in each of one or more rounds of split pool synthesis wherein the barcoded oligonucleotide in each round comprises an annealing region complementary to the annealing region of the barcode oligonucleotide from the previous round, thereby assembling cell-specific barcodes on each primer in each of the plurality of T-cells.

6. The method of claim 1, wherein the barcoding of nucleic acids in step (b) is performed by a method comprising:
(a) partitioning the population of T-cells containing nucleic acids into a plurality of first partitions containing a single cell;
(b) mixing the cell-containing partitions with a plurality of second partitions each containing multiple copies of barcoded oligonucleotide primers comprising gene-specific sequence and a barcode, wherein the barcodes are the same within each partition but differ among partitions;
(c) fusing the first and second partitions; and
(d) forming amplicons with barcoded oligonucleotide primers thereby barcoding the nucleic acids.

7. The method of claim 1, wherein the barcoding in step (b) and sequencing in step (c) are performed by a method comprising:
(a) partitioning the population of T-cells into a plurality of partitions containing groups of cells;
(b) ligating barcoded adaptors to nucleic acids in each partition;
(c) sequencing the TCRA and TCRB in the adapted nucleic acid;
(d) determining TCRA and TCRB gene pairs base on frequency of co-occurrence in partitions.

8. The method of claim 1, wherein the sequencing of barcoded TCR genes is sequencing the CDR3 hypervariable regions of the genes.

9. The method of claim 1, wherein identifying the TCR genes is identifying the CDR3 hypervariable regions of the genes.

10. The method of claim 1, wherein the tumor neoantigen genes are identified by sequencing of the nucleic acids in the tumor cell and identifying genes with non-silent mutations as tumor neoantigen genes.

11. The method of claim 1, wherein the tumor neoantigen genes are identified by screening peptide arrays with the patient's serum.

12. The method of claim 1, wherein the T-cell of step (e) lacks endogenous TCR gene expression.

13. The method of claim 1, wherein the genes in step (e) are introduced as transcriptionally active DNA fragments.

14. The method of claim 1, wherein the identified neoantigens are further selected by the ability to bind the MHC-1 molecule.

15. The method of claim 1, wherein the further barcoding the neoantigen and the TCR genes and the barcoded MHC-in the neoantigen-TCR complex comprises compartmentalizing each complex into a reaction volume containing a cell-specific barcode.

* * * * *